US012139762B2

(12) United States Patent
Hakonarson et al.

(10) Patent No.: US 12,139,762 B2
(45) Date of Patent: Nov. 12, 2024

(54) ASSOCIATION OF GENETIC VARIATIONS TO DIAGNOSE AND TREAT ATTENTION-DEFICIT HYPERACTIVITY DISORDER (ADHD)

(71) Applicant: THE CHILDREN'S HOSPITAL OF PHILADELPHIA, Philadelphia, PA (US)

(72) Inventors: Hakon Hakonarson, Malvern, PA (US); Berta Almoguera, Philadelphia, PA (US); Lyam Vazquez, Philadelphia, PA (US); Patrick Sleiman, Philadelphia, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 0 days.

(21) Appl. No.: 18/170,241

(22) Filed: Feb. 16, 2023

(65) Prior Publication Data
US 2023/0313304 A1 Oct. 5, 2023

Related U.S. Application Data

(62) Division of application No. 16/644,313, filed as application No. PCT/US2018/049722 on Sep. 6, 2018, now Pat. No. 11,591,656.

(60) Provisional application No. 62/555,523, filed on Sep. 7, 2017.

(51) Int. Cl.
C12Q 1/68 (2018.01)
C12P 19/34 (2006.01)
C12Q 1/6883 (2018.01)

(52) U.S. Cl.
CPC ..... *C12Q 1/6883* (2013.01); *C12Q 2600/136* (2013.01); *C12Q 2600/156* (2013.01)

(58) Field of Classification Search
CPC ............ C12Q 1/6883; C12Q 2600/156; C12Q 2600/136
See application file for complete search history.

(56) References Cited

U.S. PATENT DOCUMENTS

| 2004/0181048 | A1 | 9/2004 | Wang |
| 2012/0100995 | A1 | 4/2012 | Scherer et al. |
| 2014/0155271 | A1 | 6/2014 | Hatchwell et al. |
| 2014/0161721 | A1 | 6/2014 | Hatchwell et al. |
| 2014/0162894 | A1 | 6/2014 | Hatchwell et al. |
| 2017/0247762 | A1 | 8/2017 | Heiman |

OTHER PUBLICATIONS

Reference SNP (rs) Report for rs2105158, from https://www.ncbi.nlm.nih.gov/snp/rs2105158#variant_details, 10 pages printed on Jan. 22, 2024. (Year: 2024).*

International Search Report and Written Opinion, dated Jan. 8, 2019 issued in International Application No. PCT/US2018/049722, filed Sep. 6, 2018.

Faraone, Stephen V. et al., "The worldwide prevalence of ADHD: is it an American condition?," World Psychiatry, vol. 2, No. 2, Jun. 2003, pp. 104-113.

Hawi, Z. et al., "The molecular genetic architecture of attention deficit hyperactivity disorder," vol. 20, No. 3, Mar. 2015, pp. 289-297.

Mannuzza, S. et al., "Adult outcome of hyperactive boys. Educational achievement, occupational rank, and psychiatric status," Archives of General Psychiatry, vol. 50, No. 7, Jul. 1993, pp. 565-576.

Faraone, Stephen V. et al., "Attention-deficit/hyperactivity disorder in adults: an overview," Biological Psychiatry, vol. 48, No. 1, Jul. 2000, pp. 9-20.

Kessler, Ronald C. et al., "Patterns and predictors of ADHD persistence into adulthood: Results from the National Comorbidity Survey Replication," Biological Psychiatry, vol. 57, No. 11, Jun. 2005, pp. 1442-1451.

Faraone, Stephen V. et al., "Molecular genetics of attention deficit/hyperactivity disorder," Biological Psychiatry, vol. 57, No. 11, Jun. 2005, pp. 1313-1323.

Rietveld, M.J.H. et al., "Heritability of attention problems in children: I. cross-sectional results from a study of twins, age 3-12 years," American Journal of Medical Genetics, vol. 117B, No. 1, Feb. 2003, pp. 102-113.

Franke, B. et al., "The genetics of attention deficit/hyperactivity disorder in adults, a review," Molecular Psychiatry, vol. 17, No. 10, Nov. 2011, pp. 960-987.

Elia, Josephine et al., "Genome-wide copy number variation study associates metabotropic glutamate receptor gene networks with attention deficit hyperactivity disorder," Nature Genetics, vol. 44, No. 1, Jan. 2015, pp. 78-84.

Elia, Josephine et al., "Fasoracetam in adolescents with ADHD and glutamatergic gene network variants disrupting mGluR neurotransmitter signaling," Nature Communications, vol. 9, No. 1, Jan. 2018, pp. 1-9.

Neale, Benjamin M. et al., "Genome-wide Association Scan of Attention Deficit Hyperactivity Disorder," American Journal of Medical Genetics, vol. 147B, No. 8, Dec. 2008, pp. 1337-1344.

Neale, Benjamin M. et al., "Case-Control Genome-Wide Association of Attention-Deficit / Hyperactivity Disorder," Journal of the American Academy of Child and Adolescent Psychiatry, vol. 49, No. 9, Sep. 2010, pp. 906-920.

Neale, Benjamin M. et al., "Meta-analysis of genome-wide association studies of attention deficit/hyperactivity disorder," Journal of the American Academy of Child and Adolescent Psychiatry, vol. 49, No. 9, Sep. 2010, pp. 884-897.

Mick, Eric et al., "Family-Based Genome-Wide Association Scan of AttentionDeficit/Hyperactivity Disorder," Journal of the American Academy of Child and Adolescent Psychiatry, vol. 49, No. 9, Sep. 2010, pp. 898-905.

(Continued)

*Primary Examiner* — Stephen T Kapushoc
(74) *Attorney, Agent, or Firm* — Howson & Howson, LLP; Kathleen D. Rigaut; Richard F. Kane

(57) ABSTRACT

Compositions and methods for the detection and treatment of ADHD are provided.

6 Claims, 4 Drawing Sheets

Specification includes a Sequence Listing.

(56) References Cited

OTHER PUBLICATIONS

Hinney, Anke et al., "Genome-wide association study in German patients with attention deficit/hyperactivity disorder," American Journal of Medical Genetics, vol. 156B, No. 8, Dec. 2011, pp. 888-897.
Stergiakouli, Evangelia et al., "Investigating the Contribution of Common Genetic Variants to the Risk and Pathogenesis of ADHD," The American Journal of Psychiatry, vol. 169, No. 2, Feb. 2012, pp. 186-194.
Yang, Li et al., "Polygenic Transmission and Complex Neuro developmental Network for Attention Deficit Hyperactivity Disorder: GenomeWide Association Study of Both Common and Rare Variants," American Journal of Medical Genetics, vol. 162B, No. 5, Jul. 2013, pp. 419-430.
Lesch, Klaus-Peter et al., "Molecular genetics of adult ADHD: converging evidence from genome-wide association and extended pedigree linkage studies," Journal of Neural Transmission (Vienna), vol. 115, No. 11, Nov. 2008, pp. 1573-1585.
Chang, Christopher C. et al., "Second-generation PLINK: rising to the challenge of larger and richer datasets," GigaScience, vol. 4, Feb. 2015, pp. 1-16.
Das, Sayantan et al., "Next-generation genotype imputation service and methods," Nature Genetics, vol. 48, No. 10, Oct. 2016, pp. 1284-1287.
Loh, Po-Ru et al., "Reference-based phasing using the Haplotype Reference Consortium panel," vol. 48, No. 11, Nov. 2016, pp. 1443-1448.
Price, Alkes L. et al., "Principal components analysis corrects for stratification in genome-wide association studies," vol. 38, No. 8, Aug. 2006, pp. 904-909.
Marchini, Jonathan et al., "Genotype imputation for genome-wide association studies," Nature Reviews, Genetics, vol. 11, No. 7, Jul. 2010, pp. 499-511.
Ward, Lucas D. et al., "HaploReg: a resource for exploring chromatin states, conservation, and regulatory motif alterations within sets of genetically linked variants," Nucleic Acids Research, vol. 40(Database Issue), Nov. 2011, pp. D930-D934.
The GTEx Consortium, "The Genotype-Tissue Expression (GTEx) project," Nature Genetics, vol. 45, No. 6, Jun. 2013, pp. 580-585.
Ong, Bruce A., "Gene network analysis in a pediatric cohort identifies novel lung function genes," PLoS One, vol. 8, No. 9, Sep. 2013, e72899, pp. 1-7.
Ng, Bernard et al., "An xQTL map integrates the genetic architecture of the human brain's transcriptome and epigenome," Nature Neuroscience, vol. 20, No. 10, Sep. 2017, pp. 1418-1426.
Sleiman, Patrick M. A. et al., "Variants of DENND1B associated with asthma in children," The New England Journal of Medicine, vol. 362, No. 1, Jan. 2010, pp. 36-44.
Galanter, Joshua M. et al., "Genome-wide association study and admixture mapping identify different asthma-associated loci in Latinos: the Genes-environments & Admixture in Latino Americans study," The Journal of Allergy and Clinical Immunology, vol. 134, No. 2, Aug. 2014, pp. 295-305.

Lin, Ping-I et al., "No Gene Is an Island: The Flip-Flop Phenomenon," The American Journal of Human Genetics, vol. 80, No. 3, Mar. 2007, pp. 531-538.
Van Aller, Glenn S. et al., "Smyd3 regulates cancer cell phenotypes and catalyzes histone H4 lysine 5 methylation," Epigenetics, vol. 7, No. 4, Apr. 2012, pp. 340-343.
Liu, Cheng et al., "SMYD3 as an oncogenic driver in prostate cancer by stimulation of androgen receptor transcription," Journal of the National Cancer Institute, vol. 105, No. 22, Oct. 2013, pp. 1719-1728.
Zhu, Ying et al., "SMYD3 stimulates EZR and LOXL2 transcription to enhance proliferation, migration, and invasion in esophageal squamous cell carcinoma," Human Pathology, vol. 52, Jun. 2016, pp. 153-163.
Huang, Lei et al., "SET and MYND domain containing protein 3 in cancer," American Journal of Translational Research, vol. 9, No. 1, Jan. 2017, pp. 1-14.
Day, Jeremy J. et al., "DNA methylation and memory formation," Nature Neuroscience, vol. 13, No. 11, Nov. 2010, pp. 1319-1323.
Guo, Junjie U. et al., "Neuronal activity modifies the DNA methylation landscape in the adult brain," Nature Neuroscience, vol. 14, No. 10, Apr. 2012, pp. 1345-1351.
Jones, Peter A. et al., "The epigenomics of cancer," Cell, vol. 128, No. 4, Feb. 2007, pp. 683-692.
Esteller, Manel, "Epigenetics in Cancer," The New England Journal of Medicine, vol. 358, No. 11, Mar. 2008, pp. 1148-1159.
Van Bokhoven, Hans, "Genetic and epigenetic networks in intellectual disabilities," Annual Review of Genetics, vol. 45, Sep. 2011, pp. 81-104.
Ronan, Jehnna L., et al., "From neural development to cognition: unexpected roles for chromatin," Nature Reviews, Genetics, vol. 14, No. 5, May 2013, pp. 347-359.
Crawley, Jacqueline N. et al., "Autism and Cancer Share Risk Genes, Pathways, and Drug Targets," Trends in Genetics, vol. 32, No. 3, Mar. 2016, pp. 139-146.
De Araujo Lima, Leandro et al., "An integrative approach to investigate the respective roles of single-nucleotide variants and copy-number variants in Attention-Deficit/Hyperactivity Disorder," Scientific Reports, vol. 6, Mar. 2016, 22851, pp. 1-13.
Okura, Yuji et al., "Agreement between self-report questionnaires and medical record data was substantial for diabetes, hypertension, myocardial infarction and stroke but not for heart failure," Journal of Clinical Epidemiology, vol. 57, No. 10, Oct. 2004, pp. 1096-1103.
Almoguera, Berta et al., "Identification of Four Novel Loci in Asthma in European American and African American Populations," American Journal of Respiratory and Critical Care Medicine, vol. 195, No. 4, Feb. 2017, pp. 456-463.
Newton, Katherine M. et al., "Validation of electronic medical record-based phenotyping algorithms: results and lessons learned from the eMERGE network," Journal of the American Medical Informatics Association, vol. 20, No. e1, Mar. 2013, pp. e147-e154.
Non-Final Office Action, dated May 25, 2017, issued in U.S. Appl. No. 13/668,049.
Submitted SNP(ss) Details: ss218999079, submitted Jul. 20, 2011, 1 page printed from https://www.ncbi.nlm.nih.gov.

* cited by examiner

SEQUENCE LISTING

```
Sequence total quantity: 6
SEQ ID NO: 1            moltype = DNA  length = 51
FEATURE                 Location/Qualifiers
source                  1..51
                        mol_type = genomic DNA
                        organism = Homo sapiens
SEQUENCE: 1
gaggttctga gagtagtcaa actcamagag acgcaaaaca gattggtggt g            51

SEQ ID NO: 2            moltype = DNA  length = 51
```

```
FEATURE              Location/Qualifiers
source               1..51
                     mol_type = genomic DNA
                     organism = Homo sapiens
SEQUENCE: 2
aagtaaacgc ttccaagtcg gaacawccag agacatttgg ttcctctcta g         51

SEQ ID NO: 3         moltype = DNA  length = 51
FEATURE              Location/Qualifiers
source               1..51
                     mol_type = genomic DNA
                     organism = Homo sapiens
SEQUENCE: 3
cattagtaag aggtagtcag gattcraacc taagtggttt ggcatctaag t         51

SEQ ID NO: 4         moltype = DNA  length = 51
FEATURE              Location/Qualifiers
source               1..51
                     mol_type = genomic DNA
                     organism = Homo sapiens
SEQUENCE: 4
agatgtggcc aagcattctt tacacraaac aagaaacact tgcaaagcgg t         51

SEQ ID NO: 5         moltype = DNA  length = 51
FEATURE              Location/Qualifiers
source               1..51
                     mol_type = genomic DNA
                     organism = Homo sapiens
SEQUENCE: 5
cagactgcct gggtccagat cttgayacta acttgccatg tctctgtgac t         51

SEQ ID NO: 6         moltype = DNA  length = 51
FEATURE              Location/Qualifiers
source               1..51
                     mol_type = genomic DNA
                     organism = Homo sapiens
SEQUENCE: 6
cagaatatgt gtcctttcta atttgmacaa aagcactatt taagctagtg g         51
```

ASSOCIATION OF GENETIC VARIATIONS TO DIAGNOSE AND TREAT ATTENTION-DEFICIT HYPERACTIVITY DISORDER (ADHD)

CROSS-REFERENCE TO RELATED APPLICATIONS

The present application is a divisional of U.S. patent application Ser. No. 16/644,313, filed Mar. 4, 2020, now U.S. Pat. No. 11,591,656, which is a § 371 of International Application No. PCT/US2018/049722, filed Sep. 6, 2018, which claims the benefit of U.S. Provisional Application No. 62/555,523, filed Sep. 7, 2017. The entire disclosure of each of the aforesaid applications is incorporated by reference in the present application.

This invention was made with funds from the National Institutes of Health, Grant Nos. U01HG006830 and U01HG8684. The US government has certain rights in this invention.

REFERENCE TO AN ELECTRONIC SEQUENCE LISTING

The contents of the electronic sequence listing (CHOP-P06509US02.xml; Size: 6,541 bytes; and Date of Creation: Jun. 26, 2023) is herein incorporated by reference in its entirety.

FIELD OF THE INVENTION

This invention relates to the fields of genetics and the diagnosis of attention deficit hyperactivity disorder (ADHD). More specifically, the invention provides compositions and methods useful for the diagnosis and treatment of ADHD.

BACKGROUND OF THE INVENTION

Several publications and patent documents are cited through the specification in order to describe the state of the art to which this invention pertains. Each of these citations is incorporated herein by reference as though set forth in full.

Attention-deficit/hyperactivity disorder (ADHD) is the most prevalent neurobiological disorder among children, with an incidence of 6-7% that has remained stable for decades. ADHD is highly heritable, and genetic factors may account for 75%-90% of etiology. Drug treatment is not always effective, particularly in severe cases.

Studies have evaluated genetic polymorphisms or mutations that could be risk factors for developing ADHD. A large-scale, genome-wide study compared data on copy number variations (CNVs) in approximately 3,500 attention-deficit hyperactivity disorder (ADHD) cases to data from approximately 13,000 controls and found that CNVs in genes coding for metabotropic glutamate receptors (mGluR proteins or GRM genes) as well as CNVs in genes coding for proteins that interact with mGluRs occur significantly more frequently in ADHD cases compared to controls. (See WO 2012/027491 and US 2013/0203814; Elia et al., Nature Genetics, 44(1): 78-84 (2012).) Attention-deficit/hyperactivity disorder (ADHD) is the most prevalent neurobiological disorder among children, affecting 2-10% of school age children worldwide[1,2].

ADHD is characterized by clinically significant and developmentally inappropriate levels of inattention, hyperactivity, and impulsivity; and may present with predominantly inattentive or hyperactive symptoms or, more commonly, with a combination of both[2]. ADHD symptoms are associated with poor academic performance, school failure, risk for substance abuse and negative consequences for family and peer relations 3 and the disease persist into adulthood in up to 60% of the cases[2,4,5].

Twin studies show that ADHD has a heritability of 70-80% in both children and adults, which places it as the most heritable psychiatric disorder (reviewed in[6, 7, 8]). However, despite this high heritability, the underlying genetic determinants are still largely unknown. Until recently no genome-wide association studies (GWAS) or meta-analyses had unraveled any single locus surpassing the genome-wide level of significance[11,12,13,14,15, 16,17,18]. This year, the Psychiatrics Genomic Consortium (PGC) has made available on their website (http://www.med.unc.edu/pgc/) the results from the largest meta-analysis performed to date in ADHD involving 20,000 cases and 35,000 controls of European ancestry and report the identification of the first twelve loci reaching genome-wide significance.

As often seen in many complex diseases, the search for genetic factors in ADHD has focused on individuals of European ancestry, and no GWAS has been published to date involving African American (AA) subjects despite potentially higher prevalence and severity of ADHD in children of AA decent (http://adhd.psych.ac.cn/gwasStudies.do), (http://www.med.unc.edu/pgc/).

There is no cure for ADHD, but the symptoms can be managed by combinations of behavior therapy and medications. Stimulants are often misused and abused by qualifying and non-qualifying patients alike. Hence, additional ADHD medications are needed. In addition, given the genetic heterogeneity of ADHD patients, tailoring certain medication regimens to patients based on their underlying genetic profile should also improve ADHD treatment.

Contemporary and emerging treatment paradigms are ideally based on precision medicine, that is, identifying appropriate patients based on biomarkers, including genotype, with a goal of optimizing therapy while minimizing adverse events. The invention described herein addresses this need.

SUMMARY OF THE INVENTION

In accordance with the present invention, methods are provided for the diagnosis and treatment of ADHD in a genetically defined subpopulation of ADHD. An exemplary method entails detecting the presence of at least one SNP in the SMYD3 gene in a nucleic acid sample of a subject, such as, for example, rs2105158, wherein if said SNP is/are present, said subject has an increased risk for developing ADHD.

In one aspect of the present invention, a method for detecting a propensity for developing attention deficit hyperactivity disorder (ADHD) in a patient is provided. An exemplary method entails detecting the presence of at least 1, 2, 3, 4, 5 or 6 of the SNPs provided in SEQ ID NOS: 1-6, or SNPs in linkage disequilibrium with said SNPs, the presence of said SNPs being informative of the presence of increased ADHD risk. In certain embodiments, the patient is of African American ancestry and the SNP is present in the SMYD3 gene sequence. In other embodiments, patient is of European ancestry and the SNP is present in the SMYD3 gene sequence. In some embodiments, the SNP is rs2105158. In other embodiments, the sample is assessed for the presence of rs2105158, rs114359002 and rs189771980 having SEQ ID NOS: 1, 5 and 6 respectively.

In some embodiments, methods of diagnosing a subject as having ADHD are provided comprising detecting the presence or absence of at least one, two, or three of the ADHD-associated SNPs (or SNPs in linkage disequilibrium with such SNPs), and if said SNP(s) is present, diagnosing the subject as having ADHD. "ADHD-associated SNPs" are those listed in Table 6 and SEQ ID NOS: 5 and 6.

In some embodiments, methods of determining whether a subject has an increased risk for developing ADHD are provided comprising detecting the presence or absence of at least one, two, or three of the ADHD-associated SNPs (or SNPs in linkage disequilibrium with such SNPs), and if said SNP(s) is present, determining that the subject has an increased risk for developing ADHD. "ADHD-associated SNPs" are those listed in Table 6.

In one aspect of the present invention, a method for detecting a propensity for developing ADHD in a patient in need thereof is provided comprising detecting the presence or absence of at least one, two, three, four, five or six of the ADHD-associated SNPs (or SNPs in linkage disequilibrium with such SNPs), and if said SNP(s) is present, determining that the subject has an increased risk for developing ADHD. "ADHD-associated SNPs" are those listed in Table 6 and in SEQ ID NOS: 5 and 6.

In another embodiment of the invention, a method for identifying agents which alter neuronal signaling and/or morphology is provided. Such a method comprises providing cells expressing at least one nucleic acid comprising the ADHD associated SNPs of the invention, (step a); providing cells which express the cognate wild type sequences which lack the SNP (step b); contacting the cells from each sample with a test agent and analyzing whether said agent alters neuronal signaling and/or morphology of cells of step a) relative to those of step b), thereby identifying agents which alter neuronal signaling and morphology.

Methods of treating ADHD patients via administration of test agents identified using the methods described herein in patients in need thereof are also encompassed by the present invention. The invention also provides at least one isolated ADHD related SNP-containing nucleic acid selected from the group listed in SEQ ID NOS: 1-6. In one embodiment, a multiplex SNP panel containing all of the informative SNPs or SNPs in linkage disequilibrium with the same, is provided. Such SNP containing nucleic acids which indicate the presence of ADHD may optionally be contained in a suitable expression vector for expression in neuronal cells. Alternatively, they may be immobilized on a solid support. In yet another alternative, the panel may be provided in silico.

In some embodiments, methods of treating ADHD in a subject determined to have at least one ADHD-associated SNP are encompassed comprising administering to a subject a therapeutically effective amount of at least one agent useful for treating ADHD. In some embodiments, the agent is a SMYD3 modulator. In some embodiments, methods of treating ADHD in a subject are encompassed, comprising diagnosing or detecting as described above, and further administering a therapeutically effective amount of at least one agent useful for treating ADHD. In some embodiments, the agent is a SMYD3 modulator. This method provides a test and treat paradigm, whereby a patient's genetic profile is used to personalize treatment with therapeutics targeted towards specific biomarkers found in individuals exhibiting ADHD. Such a test and treat model may benefit patients with ADHD with greater efficacy and fewer side effects than non-personalized treatment.

According to yet another aspect of the present invention, there is provided a method of treating ADHD in a patient determined to have at least one prescribed single nucleotide polymorphism by administering to the patient a therapeutically effective amount of at least one modulator of SMYD3 activity, thereby alleviating ADHD symptoms. Thus, any of the patients exhibiting an alteration in SMYD3 activity can be tested for the presence of such a genetic alteration and then treated with the appropriate pharmaceutical agent.

DETAILED DESCRIPTION OF THE INVENTION

Figure 1A:
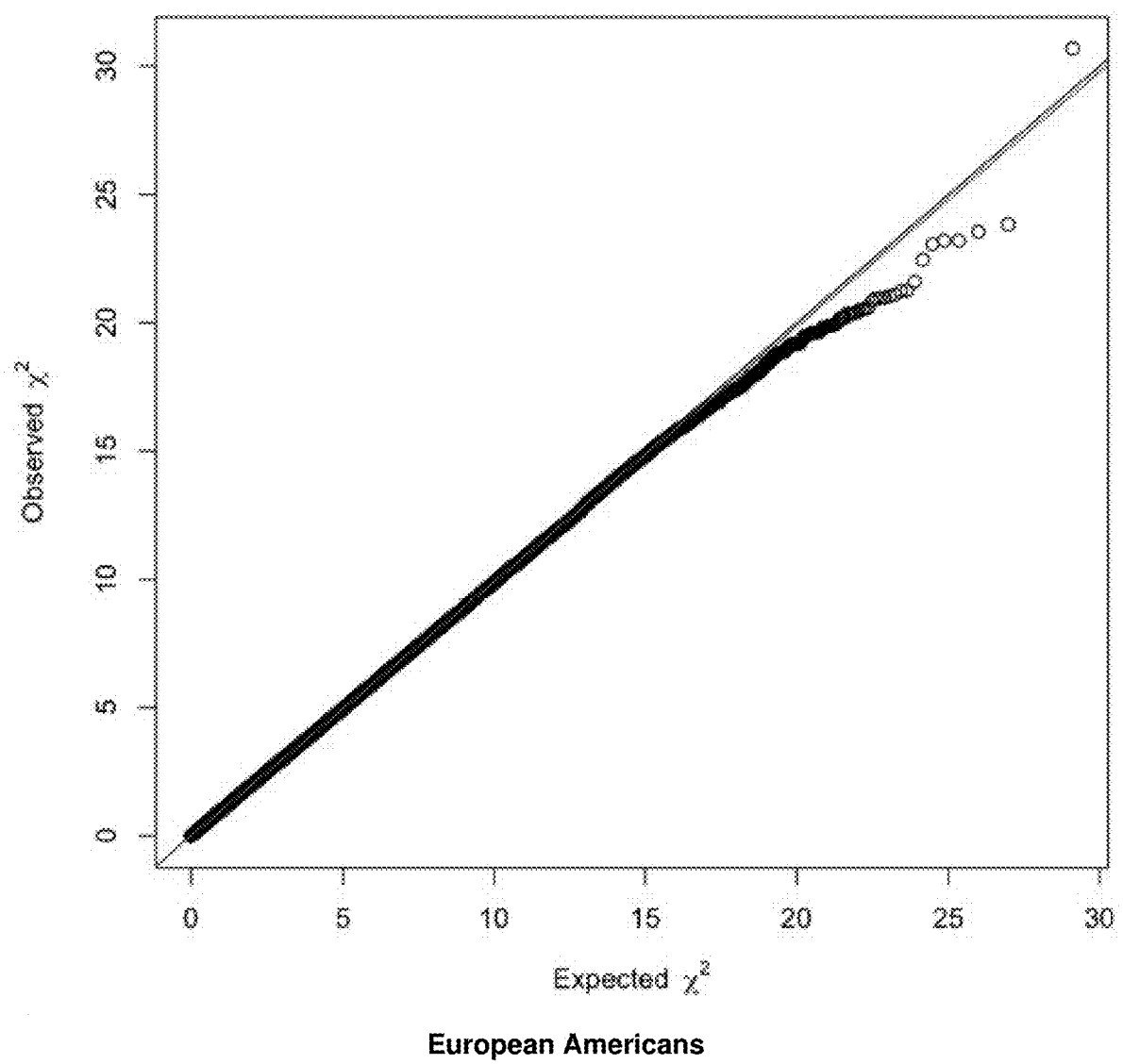
FIG. 1. Quantile-quantile plots show −log 10 (p-value) of observed genome-wide association results against expected association results for ADHD in the two samples. Genomic inflation factors are 0.996 for European Americans (FIG. 1A) and 0.999 for African Americans (FIG. 1B).

Attention-Deficit, Hyperactivity Disorder (ADHD) is a common, heritable neuropsychiatric disorder of unknown etiology. Recently, we reported an enrichment of rare variants in genes involved in learning, behavior, synaptic transmission and central nervous system development in autism, suggesting that rare inherited structural variants could also play a role in the etiology of ADHD, a related neuropsychiatric disorder.

ADHD is the most prevalent neurobiological disorder among children, with an incidence of 6-7% that has remained stable for decades. ADHD is highly heritable, and genetic factors may account for 75%-90% of the etiology. In this study, we present the first genome-wide association study (GWAS) on ADHD that includes subjects from African American (AA) ancestry (N=4,369) as well as 7,394 European Americans (EA), selected using a phenotyping algorithm designed to mine electronic health record (EHR) data and subsequently validated in an independent ADHD cohort. A GWAS of the AA sample uncovered a significant association of rs2105158 with ADHD (p-value=$5.88 \times 10^{-9}$), a variant residing in the intronic region of SMYD3, encoding a SET domain-containing histone N-lysine methyltransferase. This association replicated in the EA sample (p-value=0.033) and was also confirmed in the Psychiatric Genetic Consortium data set (p-value=$4.21 \times 10^{-3}$). The variant, rs2105158, significantly correlates with methylation values at the probe cg07311631 (p-value=$6.6 \times 10^{-19}$) located in SMYD3, in the dorsolateral prefrontal cortex, which provides support of a potential biological effect of this gene in the brain. We conclude that SMYD3, a histone methyltransferase that plays a role in transcriptional regulation as a member of RNA polymerase complexes, contributes to the pathobiology of ADHD in children of both AA and European ancestry.

The following definitions are provided to facilitate an understanding of the present invention.

I. Definitions

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

The SMYD3 gene (also referred to as KMT3E, ZMYND1, ZNFN3A1, FLJ21080, MGC104324, bA74P14.1, LOC64754 in the art) functions as a histone methyltransferase and plays a role in transcriptional regulation as a member of an RNA polymerase complex. The deduced 428-amino acid protein contains an N-terminal MYND-type zinc finger domain, followed by a SET domain. Northern blot analysis detected a 1.7-kb transcript that was specific to testis and skeletal muscle Immunohistochemical staining indicated that the subcellular localization of SMYD3 was altered by the density of cultured human hepatoma cells. In synchronized cells, SMYD3 was located mainly in the cytoplasm when the cells were arrested at G0/G1, but it accumulated in the nuclei at S phase and G2/M. SMYD3 trimethylates a lysine residue on MAP3K2, which causes crosstalk with the MAP kinase signaling pathway in Ras-driven cancers. Certain SMYD3 modulators are known in the art.

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence.

A "single nucleotide polymorphism (SNP)" refers to a change in which a single base in the DNA differs from the usual base at that position. These single base changes are called SNPs or "snips." Millions of SNP's have been cataloged in the human genome.

"ADHD-associated SNP" or "ADHD-associated specific marker" or ADHD-associated informational sequence molecule" is a SNP or marker sequence which is associated with diagnosing, determining whether a subject has an increased risk for developing, and detecting a propensity for developing ADHD, which is found in lesser frequency in normal subjects who do not have this disease. Such markers may include but are not limited to nucleic acids, proteins encoded thereby, or other small molecules. Thus, the phrase "ADHD-associated SNP containing nucleic acid" is encompassed by the above description.

"Linkage" describes the tendency of genes, alleles, loci or genetic markers to be inherited together as a result of their location on the same chromosome, and is measured by percent recombination (also called recombination fraction, or θ) between the two genes, alleles, loci or genetic markers. The closer two loci physically are on the chromosome, the lower the recombination fraction will be. Normally, when a polymorphic site from within a disease-causing gene is tested for linkage with the disease, the recombination fraction will be zero, indicating that the disease and the disease-causing gene are always co-inherited. In rare cases, when a gene spans a very large segment of the genome, it may be possible to observe recombination between polymorphic sites on one end of the gene and causative mutations on the other. However, if the causative mutation is the polymorphism being tested for linkage with the disease, no recombination will be observed.

"Centimorgan" is a unit of genetic distance signifying linkage between two genetic markers, alleles, genes or loci, corresponding to a probability of recombination between the two markers or loci of 1% for any meiotic event.

"Linkage disequilibrium" or "allelic association" means the preferential association of a particular allele, locus, gene or genetic marker with a specific allele, locus, gene or genetic marker at a nearby chromosomal location more frequently than expected by chance for any particular allele frequency in the population. Once a known SNP is identified, SNPs in linkage disequilibrium (also termed LD) may be identified via commercially available programs. For example, on the world wide web at analysistools.nci.nih.gov/LDlink/?tab=ldproxy. First, the LDproxy tab is selected. The reference rs number is entered, the r2 tab and the population of interest are selected and the SNPs in LD identified upon clicking on the "calculate" tab. A plot of surrounding area is revealed and a table with the SNPs in LD (with r2 values) is shown.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the functional and novel characteristics of the sequence.

"Target nucleic acid" as used herein refers to a previously defined region of a nucleic acid present in a complex nucleic acid mixture wherein the defined wild-type region contains at least one known nucleotide variation which may or may not be associated with ADHD but is informative of the risk of ADHD. The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately 10-6-fold purification of the native message. Thus, purification of at least one order of magnitude, preferably two or three orders, and more preferably four or five orders of magnitude is expressly contemplated. Thus the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any ADHD specific marker gene or nucleic acid, but does not hybridize to other nucleotides. Also polynucleotide which "specifically hybridizes" may hybridize only to a neurospecific specific marker, such as an ADHD-specific marker shown in the Tables contained herein. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., Molecular Cloning, Cold Spring Harbor Laboratory (1989):

$$T_m = 81.5° C. + 16.6 \text{ Log } [Na+] + 0.41(\% \ G+C) - 0.63(\% \text{ formamide}) - 600/\#bp \text{ in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide," as used herein is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 10-15, 15-25, 30, 50 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 10-15, 15-25, 30, 50 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the ADHD specific marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the ADHD specific marker nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism", or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

"Sample" or "patient sample" or "biological sample" generally refers to a sample which may be tested for a particular molecule, preferably an ADHD specific marker molecule, such as a marker described hereinbelow. Samples may include but are not limited to cells, body fluids, including blood, serum, plasma, cerebral spinal fluid, urine, saliva, tears, pleural fluid and the like.

The terms "agent" and "compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, peptides, peptide/DNA complexes, and any nucleic acid based molecule which exhibits the capacity to modulate the activity of the SNP-containing nucleic acids described herein or their encoded proteins. Agents and compounds may also be referred to as "test agents" or "test compounds" which are evaluated for potential biological activity by inclusion in screening assays described herein below.

The term "modulate" as used herein refers to increasing/promoting or decreasing/inhibiting a particular cellular, biological or signaling function associated with the normal activities of the SNP containing molecules described herein or the proteins encoded thereby. For example, the term modulate refers to the ability of a test compound or test agent to interfere with signaling or activity of a gene or protein of the present invention. In certain embodiments, the agent modulates the methyltransferase activity of SMYD3.

II. Methods of Using ADHD-Associated SNPs for Diagnosing and Detecting ADHD

The present invention provides methods of diagnosing ADHD in a patient or methods for identifying a patient having an increased risk of developing ADHD. Diagnosis, as used herein, includes not only the initial identification of ADHD associated with the genetic alterations described herein in a patient but confirmatory testing, or screening in patients who have previously been identified as having or likely to have ADHD. The methods include the steps of providing a biological sample from the patient, measuring the amount of particular sets, or any all of the ADHD associated markers (Table 6) present in the biological sample, preferably a tissue and/or blood plasma sample, and determining if the patient has a greater likelihood of ADHD based on the amount and/or type of ADHD marker expression level determined relative to those expression levels identified in patient cohorts of known outcome (e.g., a normal or control sample). A patient has a greater likelihood of having ADHD when the sample has a SNP marker expression profile associated with patients previously diagnosed with ADHD. The compositions and methods of the invention are useful for the prognosis and diagnosis and management of ADHD.

In another aspect, the patient sample may have been previously genotyped and thus the genetic expression profile in the sample may be available to the clinician. Accordingly, the method may entail storing reference ADHD associated marker sequence information in a database, i.e., those SNPs statistically associated with a more favorable or less favorable prognosis as described herein, and performance of comparative genetic analysis on the computer, thereby identifying those patients having increased risk ADHD.

ADHD-related SNP-containing nucleic acids, including but not limited to those listed below (Table 6) may be used for a variety of purposes in accordance with the present invention. ADHD-associated SNP-containing DNA, RNA, or fragments thereof may be used as probes to detect the presence of and/or expression of ADHD specific markers. Methods in which ADHD specific marker nucleic acids may be utilized as probes for such assays include, but are not limited to: (1) in situ hybridization; (2) Southern hybridization (3) northern hybridization; and (4) assorted amplification reactions such as polymerase chain reactions (PCR).

Further, assays for detecting ADHD-associated SNPs may be conducted on any type of biological sample, including but not limited to body fluids (including blood, urine, serum, gastric lavage, cerebral spinal fluid), any type of cell (such as brain cells, white blood cells, mononuclear cells, fetal cells in maternal circulation) or body tissue.

ADHD-associated SNP-containing nucleic acids, vectors expressing the same, ADHD SNP-containing marker proteins and anti-ADHD specific marker antibodies of the invention can be used to detect ADHD associated SNPs in body tissue, cells, or fluid, and alter ADHD SNP-containing marker protein expression for purposes of assessing the genetic and protein interactions involved in the development of ADHD.

In some embodiments for screening for ADHD-associated SNPs, the nucleic acid from the sample will initially be amplified, e.g. using PCR, to increase the amount of the templates. This allows the target sequences to be detected with a high degree of sensitivity if they are present in the sample. This initial step may be avoided by using highly sensitive array techniques that are important in the art.

Alternatively, new detection technologies can overcome this limitation and enable analysis of small samples containing as little as 1 µg of total RNA. Using Resonance Light Scattering (RLS) technology, as opposed to traditional fluorescence techniques, multiple reads can detect low quantities of mRNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

Any of the aforementioned techniques may be used to detect or quantify ADHD-associated SNP marker expression and accordingly, diagnose or predict likelihood of, ADHD.

III. Kits and Articles of Manufacture

Any of the aforementioned ADHD-associated SNP-containing nucleic acids can be incorporated into a kit which may also contain one or more such nucleic acids immobilized on a Gene Chip, an oligonucleotide, a polypeptide, a peptide, an antibody, a non-naturally occurring detectable label, marker, reporter, a pharmaceutically acceptable carrier, a physiologically acceptable carrier, instructions for use, a container, a vessel for administration, an assay substrate, or any combination thereof. In some embodiments, the nucleic acids are immobilized on the solid support or Gene Chip such that they are not removable from the support.

IV. Methods of Using ADHD-Associated SNPs for the Development of Therapeutic Agents Since the SNPs identified herein have been associated with the etiology of ADHD, methods for identifying agents that modulate the activity of the genes and their encoded products containing such SNPs should result in the generation of efficacious therapeutic agents for the treatment of this disorder.

Several regions of the human genome provide suitable targets for the rational design of therapeutic agents. Small nucleic acid molecules or peptide molecules corresponding to these regions may be used to advantage in the design of therapeutic agents that effectively modulate the activity of the encoded proteins.

Molecular modeling should facilitate the identification of specific organic molecules with capacity to bind to the active site of the proteins encoded by the SNP-containing nucleic acids based on conformation or key amino acid residues required for function. A combinatorial chemistry approach will be used to identify molecules with greatest activity and then iterations of these molecules will be developed for further cycles of screening.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as described above) which have a nonfunctional or altered ADHD associated gene. These host cell lines or cells are defective at the polypeptide level. The host cell lines or cells are grown in the presence of drug compound. Altered glutaminergic function of the host cells is measured to determine if the compound is capable of regulating this function in the defective cells. Host cells contemplated for use in the present invention include but are not limited to bacterial cells, fungal cells, insect cells, mammalian cells, and plant cells. However, mammalian cells, particularly neuronal cells are preferred. The ADHD-associated SNP encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

A wide variety of expression vectors are available that can be modified to express the novel DNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in *Saccharomyces* are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/V5&His (Invitrogen); baculovirus vectors such as pVL1392, pVL1393, or pAC360 (Invitrogen); and yeast vectors such as YRP17, YIPS, and YEP24 (New England Biolabs, Beverly, Mass.), as well as pRS403 and pRS413 Stratagene Inc.); Picchia vectors such as pHIL-D1 (Phillips Petroleum Co., Bartlesville, Okla. 74004); retroviral vectors such as PLNCX and pLPCX (Clontech); and adenoviral and adeno-associated viral vectors.

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, Picchia promoters such as the alcohol oxidase promoter, and *Saccharomyces* promoters such as the ga14 inducible promoter and the PGK constitutive promoter, as well as neuronal-specific platelet-derived growth factor promoter (PDGF), the Thy-1 promoter, the hamster and mouse Prion promoter (MoPrP), and the Glial fibrillar acidic protein (GFAP) for the expression of transgenes in glial cells.

In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the ADHD-associated SNPs of the present invention or functional fragments thereof provide a system in which to screen potential compounds or agents for the ability to modulate the development of ADHD. Thus, in one embodiment, the nucleic acid molecules of the invention may be used to create recombinant cell lines for use in assays to identify agents which modulate aspects of cellular metabolism associated with ADHD and aberrant glutaminergic function. Also provided herein are methods to screen for compounds capable of modulating the function of proteins encoded by SNP-containing nucleic acids.

Another approach entails the use of phage display libraries engineered to express fragment of the polypeptides encoded by the SNP-containing nucleic acids on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based.

One can bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved polypeptide activity or stability or which act as inhibitors, agonists, antagonists, etc. of polypeptide activity. By virtue of the availability of SNP-containing nucleic acid sequences described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

In another embodiment, the availability of ADHD-associated SNP-containing nucleic acids enables the production of strains of laboratory mice carrying the ADHD-associated SNPs of the invention. Transgenic mice expressing the ADHD-associated SNP of the invention provide a model system in which to examine the role of the protein encoded by the SNP-containing nucleic acid in the development and progression towards ADHD. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role that a target protein plays in various cellular metabolic processes, including: aberrant glutaminergic function, altered neuroactive ligand receptor signaling and aberrant neurotransmission, or altered neuronal morphology and neurite outgrowth. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of ADHD-associated SNP-containing nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated ADHD-associated SNP genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels 105-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabino-fluranosyl)-5-iodou-racil, (FIAU). By this counter selection, the number of homologous recombinants in the surviving transformants can be increased. Utilizing ADHD-associated SNP-containing nucleic acid as a targeted insertional cassette provides means to detect a successful insertion as visualized, for example, by acquisition of immunoreactivity to an antibody immunologically specific for the polypeptide encoded by ADHD-associated SNP nucleic acid and, therefore, facilitates screening/selection of ES cells with the desired genotype.

As used herein, a knock-in animal is one in which the endogenous murine gene, for example, has been replaced with human ADHD-associated SNP-containing gene of the invention. Such knock-in animals provide an ideal model system for studying the development of ADHD.

As used herein, the expression of a ADHD-associated SNP-containing nucleic acid, or an ADHD-associated fusion protein in which the SNP is encoded can be targeted in a "tissue specific manner" or "cell type specific manner" using a vector in which nucleic acid sequences encoding all or a portion of an ADHD-associated SNP are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific proteins are well known in the art and described herein.

The nucleic acid sequence encoding the ADHD-associated SNP of the invention may be operably linked to a variety of different promoter sequences for expression in transgenic animals Such promoters include, but are not limited to a prion gene promoter such as hamster and mouse Prion promoter (MoPrP), described in U.S. Pat. No. 5,877, 399 and in Borchelt et al., Genet. Anal. 13(6) (1996) pages 159-163; a rat neuronal specific enolase promoter, described in U.S. Pat. Nos. 5,612,486, and 5,387,742; a platelet-derived growth factor B gene promoter, described in U.S. Pat. No. 5,811,633; a brain specific dystrophin promoter, described in U.S. Pat. No. 5,849,999; a Thy-1 promoter; a PGK promoter; a CMV promoter; a neuronal-specific platelet-derived growth factor B gene promoter; a NEGR1 promoter, a GRMS promoter, a promotor of any gene listed in the tables below, and Glial fibrillar acidic protein (GFAP) promoter for the expression of transgenes in glial cells.

Methods of use for the transgenic mice of the invention are also provided herein. Transgenic mice into which a nucleic acid containing the ADHD-associated SNP or its encoded protein have been introduced are useful, for example, to develop screening methods to screen therapeutic agents to identify those capable of modulating the development of ADHD.

V. Pharmaceutical and Peptide Therapies

In some embodiments, methods for treating ADHD are provided comprising administering an agent useful in the treatment of ADHD to a subject having one or more SNPs recited in Table 6, or a SNP in linkage disequilibrium with one or more of these SNPs. Such agents include without limitation, modulators of SMYD3 methyltransferase activity. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

In each of the method of treating embodiments described above, the method may further comprise detecting or diagnosing the subject prior to treatment, wherein the detection or diagnosing comprises detecting one or more SNPs recited in Table 6, or a SNP in linkage disequilibrium with one or more of these SNPs.

In each of the method of treating embodiments described above, the method may further comprise administering a second agent that is the same or different from the first agent, each agent being any agent known to those of skill to be useful in the treatment of ADHD. The second agent may be administered at the same time or after the first agent.

The materials and methods set forth below are provided to facilitate the practice of the following examples.
Assessment of Phenotype and Study Subjects This project was approved by the IRBs at The Children's Hospital of Philadelphia (CHOP). Written informed consent was obtained from each participant in accordance with institutional requirements and the Declaration of Helsinki Principles.

ADHD cases and controls were identified using a phenotyping algorithm that mines EMR data for pertinent combination of diagnostic and medication information. The algorithm defined cases as children four years or older and having either 1) two or more ICD9 codes for ADHD (314.1-314.9) in two separate in-person visits and more than two prescriptions of ADHD-related medications (Table 1), or 2) three or more ICD9 codes for ADHD on separate calendar days. Exclusion criteria were applied to cases for conditions related to brain anomalies or tumors, mental retardation, or psychiatric disorders (Table 2). Controls were defined as children four years or older with no ICD9 codes for ADHD or other psychiatric, neurological and related disorders (Table 3); no mention of the terms "ADHD", "attention deficit", "hyperkinesia", "hyperkinesis", "hyperkinetic", or "hyperactivity"; and no ADHD related medication (Table 1).

TABLE 1

Medications used in the inclusion criteria for ADHD cases and as exclusionary criteria for ADHD controls.

| Medication type | Compound |
| --- | --- |
| Stimulants | Methylphenidate, dexmethylphenidate, amphetamines |
| Norepinephrine reuptake inhibitors | Atomoxetine |
| Alpha-2 Agonists | Clonidine, guanfacine |
| Norepinephrine-dopamine reuptake inhibitors | Bupropion |
| Serotonin and norepinephrine reuptake inhibitors (SNRIs) | Imipramine, melipramine |
| Other drugs | Carbamazepine, clonazepam, fluoxetine, hydroxyzine, lithium, olanzapine, paroxetine, pemoline, risperidone, sertraline, trazodone, valproic acid. |

TABLE 2

Exclusionary ICD9 codes applied to ADHD cases
Psychiatric and Related

| ICD-9 Codes | Diagnosis |
| --- | --- |
| 290-299.x | Psychoses |
| 300.6x | Depersonalization disorder |
| 300.8x | Somatoform disorders |
| 301-301.x | Personality disorders |
| 303-303.x | Alcohol dependence syndrome |
| 304-304.x | Drug dependence |
| 307.2x | Tics |
| 307.3x | Stereotypic movement disorder |
| 317-317.x | Mild mental retardation |
| 318-318.x | Other specified mental retardation |
| 319-319.x | Unspecified mental retardation |
| | General |
| 006.5 | Amebic brain abscess |
| 013.2 | Tuberculoma of brain |
| 191-191.x | Malignant neoplasm of brain |
| 192-192.x | Malignant neoplasm of other and unspecified parts of nervous system |
| 237.7x | Neurofibromatosis |
| 290.1 | Presenile dementia |
| 348.1 | Anoxic brain damage |
| 348.2 | Benign intracranial hypertension |
| 348.3 | Encephalopathy, not elsewhere classified |
| 348.4 | Compression of brain |
| 348.5 | Cerebral edema |
| 348.8 | Other conditions of brain |
| 348.9 | Unspecified condition of brain |
| 437.2 | Hypertensive encephalopathy |
| 742-742.x | Other congenital anomalies of nervous system |
| 764-764.x | Slow fetal growth and fetal malnutrition |
| 767.0 | Subdural and cerebral hemorrhage |
| 767.9 | Birth trauma, unspecified |
| 800-804 | Fracture of skull |
| 959.01 | Head injury, unspecified |

TABLE 3

List of exclusionary ICD9 codes applied to ADHD controls.

| ICD-9 Codes | Diagnosis |
|---|---|
| 006.5 | Amebic brain abscess |
| 013.2 | Tuberculoma of brain |
| 191-191.x | Malignant neoplasm of brain |
| 192-192.x | Malignant neoplasm of other and unspecified parts of nervous system |
| 237.7x | Neurofibromatosis |
| 290-319.x | Mental disorders |
| 327-327.x | Organic sleep disorders |
| 330-337.x | Hereditary and degenerative diseases of the central nervous system |
| 342-342.x | Hemiplegia and hemiparesis |
| 343-343.x | Infantile cerebral palsy |
| 344-344.x | Other paralytic syndromes |
| 345-345.x | Epilepsy and recurrent seizures |
| 347-347.x | Cataplexy and narcolepsy |
| 348-348.x | Other conditions of brain |
| 349-349.x | Other and unspecified disorders of the nervous system |
| 437.2 | Hypertensive encephalopathy |
| 742-742.x | Other congenital anomalies of nervous system |
| 764-764.x | Slow fetal growth and fetal malnutrition |
| 765-765.x | Disorders relating to short gestation and low birthweight |
| 767.0 | Subdural and cerebral hemorrhage |
| 767.9 | Birth trauma, unspecified |
| 779.4 | Drug reactions and intoxications specific to newborn |
| 779.5 | Drug withdrawal syndrome in newborn |
| 781-781.x | Symptoms involving nervous and musculoskeletal systems |
| 800-804 | Fracture of skull |
| 959.01 | Head injury, unspecified |
| 996.2 | Mechanical complication of nervous system device, implant, and graft |

The algorithm was validated internally and also externally at an eMERGE site, Cincinnati Children's Hospital and Medical Center (CCHMC), by manual chart review of 100 randomly selected cases (N=50) and controls (N=50). Positive predictive values (PPVs) for cases and controls were then calculated for the two samples.

ADHD cases and controls for the study were selected from the biorepository at the Center for Applied Genomics (CAG). CAG has a collection of over 90,000 internal pediatric samples genotyped using standard genome-wide arrays from Illumina and Affymetrix and linked to their electronic health records (EHRs). All subjects have consented to analyses and EHR mining from the full longitudinal record, which has a mean duration>5.5 years/subject. Mean age of these subjects is 11 years and 47% are of EA ancestry, 43% AA and 10% from other ancestry groups. An additional sample of ADHD cases and controls was accrued at CCHMC as part of the eMERGE-II project (https://emerge.mc.vanderbilt.edu/) and used in the analysis.

Genotype Imputation and Population Stratification Assessment

At CAG, imputed genotypes were extracted from a collection of 36,000 subjects, genotyped on a variety of Illumina chips: Illumina Human610-Quad version 1, Illumina Hap550, Illumina Infinium Global Screening Array, and Illumina OmniExpress arrays (Supplemental Table 4). Prior to imputation, PLINK[19] was used for quality control of the data, which included removing variants with minor allele frequency (MAF)<1% and missing from 5% of samples, and samples missing >5% of SNPs. Imputation was performed on each chip type separately on the Michigan Imputation Server[20] against release 1.1 of the Haplotype Research Consortium (HRC) reference panel[21]. Poorly imputed variants defined by a 'R$^2$' score<0.5 were removed.

TABLE 4

CAG samples included in the analysis by ancestry and chip type.

| | Controls | Cases | Total |
|---|---|---|---|
| AA | 3,654 | 714 | 4,368 |
| Human610-Quad | 1,728 | 317 | 2,045 |
| Hap550 | 1,395 | 296 | 1,691 |
| Global Screening Array | 531 | 101 | 632 |
| EA | 6,015 | 938 | 6,953 |
| Human610-Quad | 2,623 | 407 | 3,030 |
| Hap550 | 2,555 | 374 | 2,929 |
| OmniExpress | 837 | 157 | 994 |
| Total | 9,669 | 1,652 | 11,321 |

For principal component analysis, we used Eigenstrat 3.0[22] on a set of 130,000 linkage disequilibrium (LD)-pruned SNPs overlapping between the Illumina Human610-Quad, Hap550, and OmniExpress arrays, that were extracted from the imputed files. Samples were separated into AA and EA based on the first two principal components using a k-means clustering analysis. Ten principal components were re-generated for each cohort and included as covariates to control for population stratification in each individual analysis.

Cryptic relatedness and duplicated samples were assessed by pairwise Identity-By-Descent values (PLINK) calculated on the same set of 130,000 SNPs and a random sample from each pair was removed.

ADHD cases and controls from CCHMC were extracted from a sample of 83,717 subjects imputed by the eMERGE-III Coordinating Center that also used the Michigan Imputation Server, the minimac3 algorithm and the Haplotype Reference Consortium 1.1 panel for the imputation. A threshold of 2% was applied for sample and SNP missingness.

For population stratification analysis, the eMERGE-III Coordinating Center used PLINK2 to perform a PCA on the 83,717 subjects with variants with MAF>5%, missingness<0.1 and LD pruned to an R$^2$ threshold of 0.7.

Association Analysis

For the CAG sample, we used BCFtools (https://samtools.github.io/bcftools/) to extract the study samples from the imputed data. VCF files were then converted to the Oxford format (gen/sample) using PLINK[19] to be used by SNPTEST[23] for the association analysis. Samples from each chip type and ancestry were analyzed separately with ten principal components and gender as covariates.

The CCHMC sample was analyzed using PLINK[19] adjusting by the same covariates as well as chip type. Variants with a MAF≤1%, R$^2$<0.5 (R$^2$<0.7 for CCHMC) and variants not meeting Hardy-Weinberg equilibrium in controls (p-value<5×10$^{-8}$ for CAG's sample and 10$^{-3}$ for CCHMC) were removed from the analysis.

Results from the two cohorts were meta-analyzed in the EA and AA using an inverse variance fixed effects method with METAL, with control for genomic inflation.

The results from the ADHD GWAS recently performed by the PGC, which are publicly available at http://www.med.unc.edu/pgc/results-and-downloads, were used to confirm the genetic associations found in our cohort. Cis-expression quantitative trait locus (eQTL) effect was investigated for all significant variants by mining HaploReg v4[24], the NCBI Genotype-Tissue Expression (GTEx) version 6[25] in brain, BRAINEAC (http://caprica.genetics.kcl.ac.uk/BRAINEAC/)[26] and the CommonMind Consortium Knowledge Portal (https://www.synapse.org/#!Synapse:syn2759792/wild/69613). Methylation quantitative trait locus (mQTL) effects in the dorsolateral prefrontal cortex of the brain were assessed by querying the Brain xQTL Serve (http://mostafavilab.stat.ubc.ca/xQTLServe/)[27].

The Examples below are provided to illustrate certain embodiments of the invention. They are not intended to limit the invention in any way.

Example I

Validation of the ADHD Algorithm and Characteristics of the Study Sample

The ADHD algorithm was validated by manual chart review internally at CAG and yielded PPVs of 96% for both cases and controls. Secondary validation was performed at CCHMC and the predictive values were 89% and 95%, for cases and controls, respectively. The implementation of the algorithm accrued 3,504 cases and 18,785 controls in CAG's biorepository. Of the total 22,289 samples, 13,156 had genotyping data, 825 samples were removed due to cryptic relatedness or duplicated samples and PCA analysis classified 4,368 as AA (714 cases and 3,654 controls) and 6,953 as EA (938 cases and 6,015 controls) that were included in the final analysis (N=11,321, Table 5, and Table 4).

Implementation of the algorithm by CCHCM accrued 92 cases and 349 controls of European ancestry with imputed data that were used for the analysis (92 cases and 349 controls).

TABLE 5

Total number of ADHD cases and controls of EA and AA ancestry included in the GWAS

|  | Controls | Cases | Total |
|---|---|---|---|
| Total samples at CAG |  |  | 11,321 |
| European American | 6,015 | 938 | 6,953 |
| African American | 3,654 | 714 | 4,369 |
| Samples at CCHMC (European American) | 349 | 92 | 441 |
| Total | 10,019 | 1,744 | 11,763 |

Figure 1B:
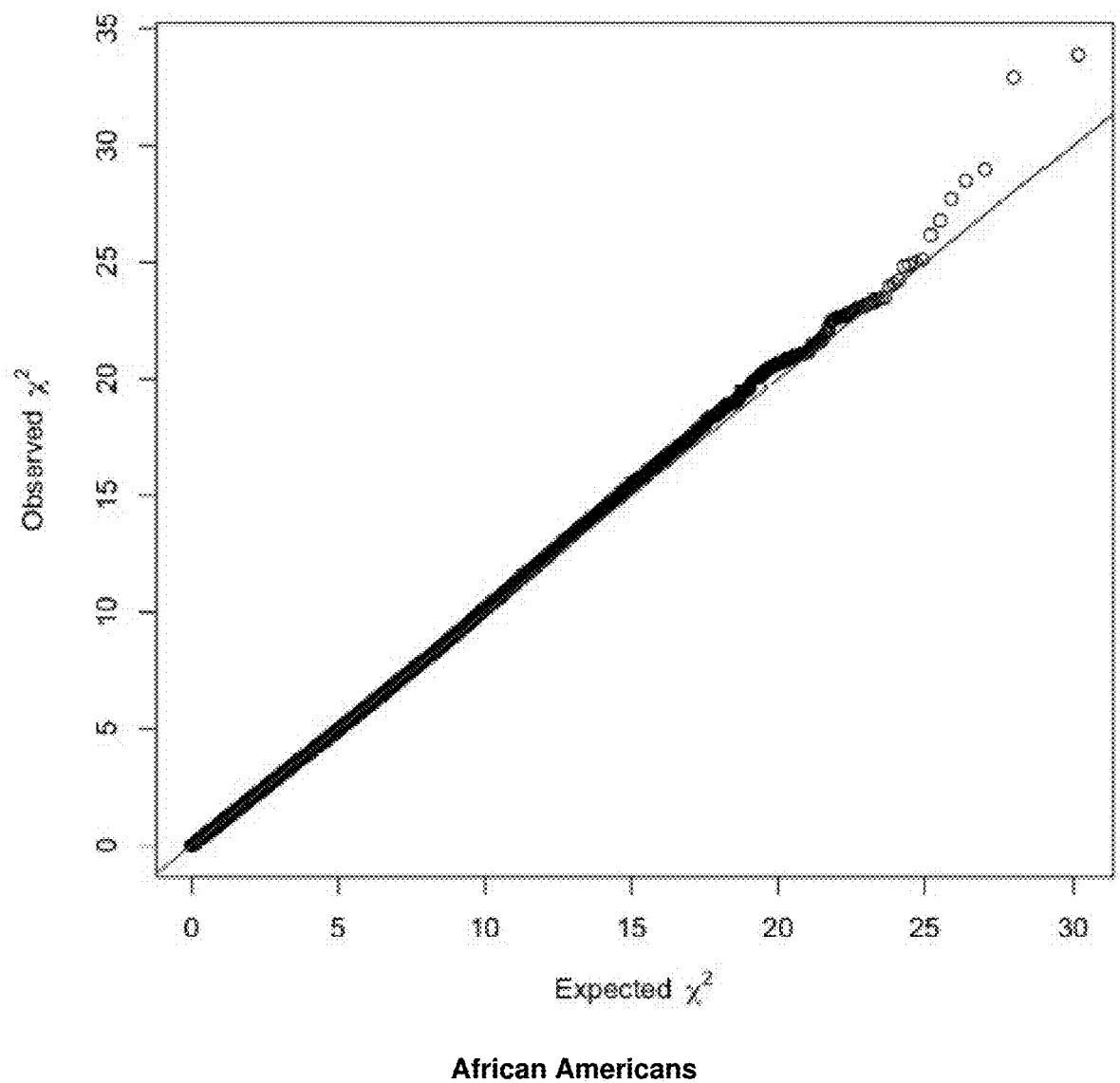

An Intronic Variant in SMYD3 Significantly Associates with ADHD in the AA Population and Replicates in EA GWASs were performed separately on each of the chip types and ancestry adjusting by sex and ten first principal components in the CAG sample and also by chip type in the CCHMC sample, and results were then meta-analyzed in the EA and AA samples. Genomic inflation factors were 0.996 and 0.999 in EA and AA, respectively (FIG. 1).

The GWAS on the EA sample included 7,275,402 variants with MAF>1% and did not yield any genome wide significant result. The top association was rs11610408 (beta(SE)= 0.569 (0.106); p-value=$8.755 \times 10^{-8}$, MAF=0.057) in the intronic region of the gene HCAR1, which encodes the hydroxycarboxylic acid receptor 1. This variant was not present in the PGC results data set so could not be assessed for replication but did not replicate in our AA sample (p-value=0.348).

Figure 2A:
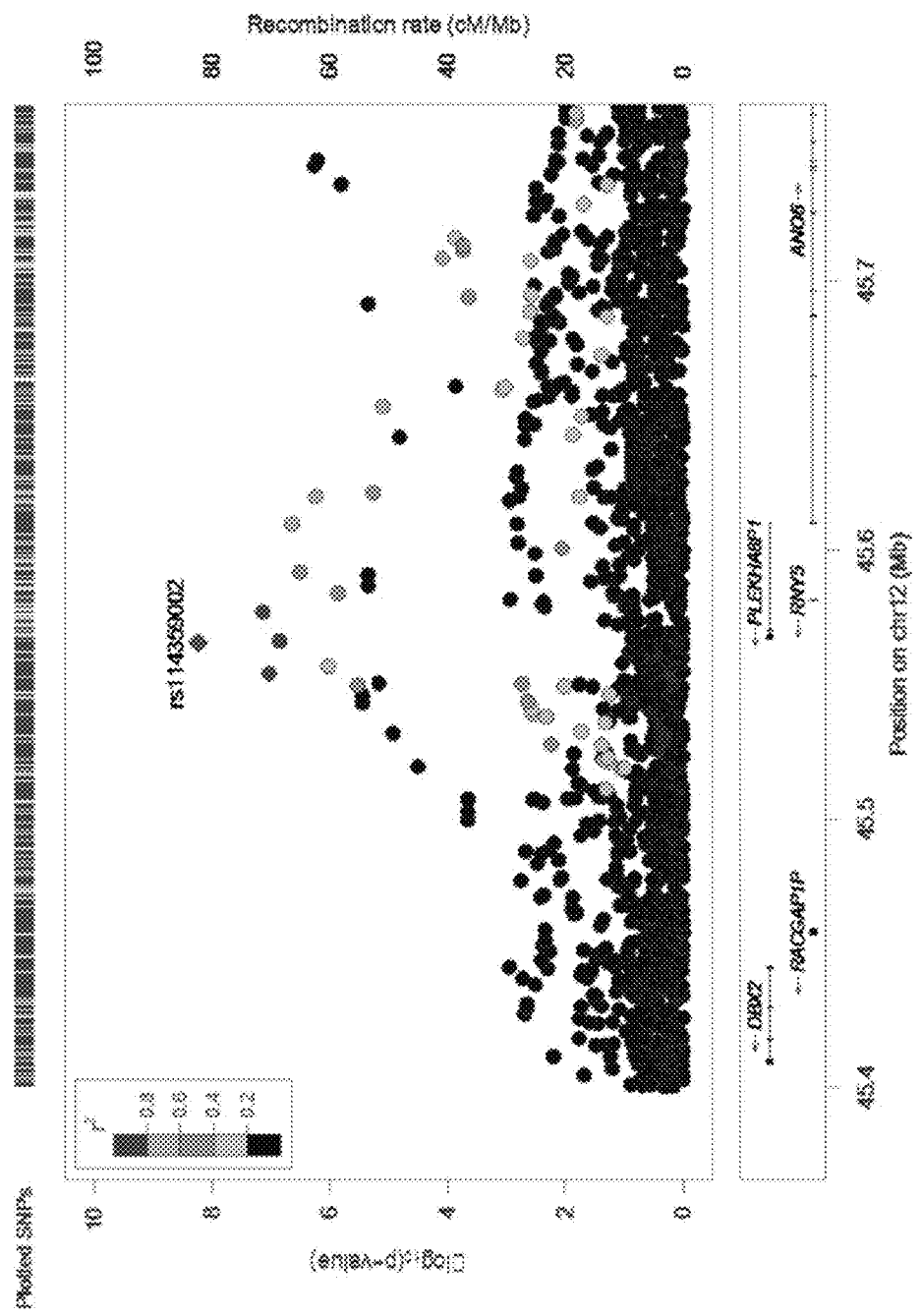
FIG. 2. Regional association plots of the two loci associated with ADHD in African Americans in chromosomes 12 (FIG. 2A) and 1 (FIG. 2B). Statistical significance of each SNP on the −log 10 (p-value) scale as a function of chromosome position in the meta-analyses. The top SNP at each locus is shown with the correlations ($r^2$) of surrounding SNPs indicated by color as illustrated in the figure. Grey represents unknown $r^2$. The fine scale recombination rate is shown on the right side of the plots.
Figure 2B:
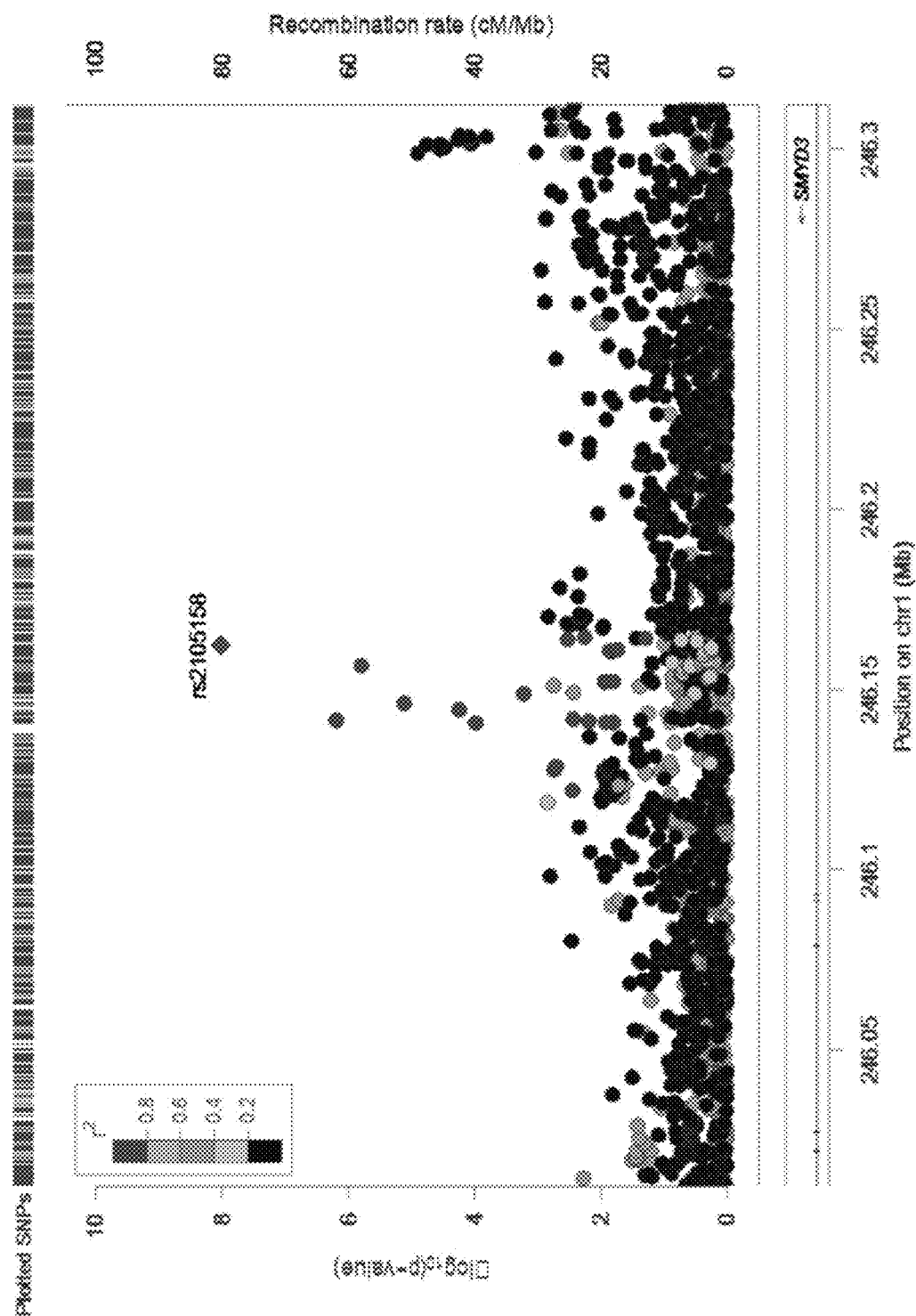

In the AA cohort, the analysis of 12,593,930 variants identified two loci surpassing the genome-wide significance threshold of $5 \times 10^{-8}$ (FIG. 2): rs114359002 (beta (SE)=0.689 (0.118); p-value=$5.88 \times 10^{-9}$) 1.4 kb 3' of PLEKHA8P1 (pleckstrin homology domain containing, family A member 8 pseudogene 1) and 44 kb 5' of ANO6 (anoctamin 6); and rs2105158 in the intronic region of SMYD3, encoding the SET and MYND domain containing 3 gene (Table 6, FIG. 2).

As shown in Table 6, rs2105158 in SMYD3 and variants in LD with rs2105158, associated with ADHD with p<$10^{-5}$, and replicated in the EA sample (beta (standard error)=− 0.163 (0.077); p-value=0.033 and MAF=0.117) and in the PGC data set (OR=0.942 (SE=0.021); p=$4.2 \times 10^{-3}$), which includes 20,183 cases and 35,191 controls of European and Asian ancestry (on the world wide web at med.unc.edu/pgc/; unpublished data). For both EA cohorts the direction of effect was opposite to that seen in AA, as is known to occur with disease associated alleles of African ancestry[28]. rs114359002 had a very low frequency in the EA sample (MAF=0.07%) and this variant was not present in the PGC data.

TABLE 6

Association of rs2105158 and SNPs in LD with p-values <$10^{-5}$ in African Americans, Europeans and in the PGC. P-values from the mQTL effects reported in the Brain xQTL Serve for probe cg07311631 are also presented.

| SNP | Position | P-value African Americans | P-value European Americans | P-value Psychiatric Genomics Consortium | p-value mQTL effect in brain |
|---|---|---|---|---|---|
| rs2105158 | 1:246162256 | $9.63 \times 10^{-9}$ | 0.033 | $4.21 \times 10^{-3}$ | $6.60 \times 10^{-19}$ |
| rs12042146 | 1:246141458 | $6.34 \times 10^{-7}$ | 0.026 | $5.95 \times 10^{-3}$ | $2.19 \times 10^{-17}$ |
| rs7548294 | 1:246156599 | $1.59 \times 10^{-6}$ | 0.033 | $4.23 \times 10^{-3}$ | $6.64 \times 10^{-19}$ |
| rs1538293 | 1:246146178 | $7.60 \times 10^{-6}$ | 0.040 | $7.54 \times 10^{-3}$ | $2.48 \times 10^{-18}$ |

ADHD associated SNPs and flanking sequences are provided below.

```
rs2105158
                                                  (SEQ ID NO: 1)
GAGGTTCTGAGAGTAGTCAAACTCA[A/C]AGAGACGCAAAACAGATTG
GTGGTG rs12042146
                                                  (SEQ ID NO: 2)
AAGTAAACGCTTCCAAGTCGGAACA[A/T]CCAGAGACATTTGGTTCCT
CTCTAG rs7548294
                                                  (SEQ ID NO: 3)
CATTAGTAAGAGGTAGTCAGGATTC[A/G]AACCTAAGTGGTTTGGCAT
CTAAGT rs1538293
                                                  (SEQ ID NO: 4)
AGATGTGGCCAAGCATTCTTTACAC[A/G]AAACAAGAAACACTTGCAA
AGCGGT rs114359002
                                                  (SEQ ID NO: 5)
CAGACTGCCTGGGTCCAGATCTTGA[C/T]ACTAACTTGCCATGTCTCT
GTGACT rs189771980
                                                  (SEQ ID NO: 6)
CAGAATATGTGTCCTTTCTAATTTG[A/C]ACAAAAGCACTATTTAAGC
TAGTGG
``` eQTL and mQTL effects were explored for the variants significantly associated with ADHD in AA. In the Brain xQTL Serve (http://mostafavilab.stat.ubc.ca/xQTLServe/), rs2105158 was significantly associated with the methylation values at the probe cg07311631 (Spearman Rho=0.395; p-value=$6.6 \times 10^{-19}$), which is located 13.3 kb from rs2105158, in SMYD3 (chr12:246148901). No eQTL effects were reported in this database for this variant but BRAINEAC, HaploregV4 and GTEx reported slight eQTL effects for rs2105158 and an increased expression of SMYD3 in other parts of the brain (frontal cortex p-value=$8.50 \times 10^{-3}$ and thalamus p-value=$7.60 \times 10^{-3}$ in BRAINEAC).

Discussion

Until the recent identification of the first twelve loci in ADHD by the PGC, no single GWAS or meta-analysis had uncovered loci with SNVs surpassing the genome-wide significant threshold[11,12,13,14,15,16,17,18]. The large sample size included in the PGC data set, with over 20,000 cases and 35,000 controls of European and Asian ancestry, has undoubtedly contributed to these findings. In the present work, we report the first ADHD GWAS that includes individuals of AA ancestry along with EA. The inclusion of AAs has revealed SMYD3 as the first locus that is significantly associated with ADHD in this population and replicating in cases of EA ancestry, both from our internal ADHD sample well as from the PGC data set. We were not able to confirm the recently reported loci by the PGC nor identify any association in the EA sample, which could be attributed to the relatively small sample size investigated in the present study. It should be noted that the effect of rs2105158 was opposite in AA and EA. This reversed effect has been previously reported in asthma[28,29] and other traits and it can be attributed to differences in the underlying genomic architecture between the two study populations[30].

SMYD3 is a SET domain-containing histone N-lysine methyltransferase (also known as KMT3E) that methylates histone H3 at lysine 4 (H3K4), and histone 4 at lysine 5 (H4K5)[31] and regulates gene expression. It also binds to the regulatory regions of target genes, regulating their transcription[32,33], and is a crucial element in a range of cellular processes like cell viability, growth, proliferation or adhesion[34]. SMYD3 is a well-established cancer gene, with an essential role in tumor cell growth and increased expression in various cancer types[34]. Expression data indicate that SMYD3 is highly expressed in brain from human tissues[25,26].

Histone methylation plays key roles in alteration of chromatin structure, resulting in the regulation of DNA replication and gene expression, and in brain, epigenetic processes control several neurobiological and cognitive functions, from early brain development and neurogenesis to memory formation, learning and synaptic plasticity[35,36]. Epigenetic alterations, such as disruption of histone modifiers, are known contributors to the initiation and progression of cancer[37,38] but are also increasingly being implicated in neurodevelopmental and psychiatric disorders[39,40]. Indeed, a number of these epigenetic alterations are shared between the three conditions[40,41] The hypothesis behind this overlap is that errors associated with genome maintenance during fetal life might affect prenatal brain development, resulting in neurodevelopmental disorders, whereas errors leading to cancer more commonly occur during adult life in cell types susceptible to tumors[41].

In a paper recently published by Ng et al[27], the authors reported a significant correlation between rs2105158, the top SMYD3 variant from this study, and increased methylation levels on SMYD3 on the dorsolateral prefrontal cortex of the brain 27, which provides support of a functional role of this variant in SMYD3 and a potential effect of this gene in brain and ADHD. Indeed, SMYD3 has already emerged as a candidate gene for ADHD[42]. In a study by Lima and colleagues, the authors used an integrative approach to determine the combined contribution of single nucleotide and copy number variants to the ADHD phenotype and built a protein-protein interaction network using 30 genes selected based on the type of variants they harbored. SMYD3 was one of the 30 seed genes in the network[42].

For the present study, cases and controls were selected using an electronic phenotyping algorithm designed to mine EHR data for appropriate ICD9 codes and medications. Leveraging EHRs, we are able to systematically apply exclusions related to a co-morbid diagnosis of epilepsy, low IQ, other neurological disorders, and other genetic/medical disorders associated with (endo)phenotypes that can mimic ADHD, but in the context of cataloged medical history, as opposed to self-report, which can be variable 43. This same approach can be applied to controls as well as cases, where we have an opportunity to additionally exclude etiologies that are potentially confounding or have documented comorbidity with ADHD. Further, the EHRs used here also contain full and longitudinal medication histories, which we leverage to optimize selection of cases/controls. In this context, drug history can be used as a proxy for a confounding exclusionary diagnosis (e.g. lithium for mood disorders), to provide more stringent exclusions on controls (i.e. controls are required to have no history of an ADHD-relevant medication), and to bolster selection of cases (i.e. for cases with an incomplete diagnostic history (<3 ADHD-related EHR encounters) history of ADHD medication is also required. This phenotyping approach has demonstrated to be accurate for case/control selection[44,45] and has been successfully used by our group and others in the search of genetic determinants of complex disorders[44,45].

Two ethnic-specific associations (FIG. 1), including rs114359002 at chr 12 in the region between the genes ANO6 and PLEKHABP1 ($p=5.88\times10^{-9}$) and rs189771980, downstream of EFEMP1 ($p=4.27\times10^{-8}$) at chromosome 2 were also identified in the AA cases. These variants were not found in the EA sample alone.

In summary, we have identified a novel locus at SMYD3 that is significantly associated with ADHD in AA children and which is replicated in cases of EA ancestry. We have also identified novel SNPs rs114359002 and rs189771980 that are significantly associated with ADHD in AA children. This information provides new therapeutic avenues and targets for ameliorating symptoms of ADHD.

Example II

Multiplex SNP Panel for Diagnosis of ADHD

As described above in Example I, several genetic alterations have been found to be associated with the ADHD phenotype. The information herein above can be applied clinically to patients for diagnosing an increased susceptibility for developing ADHD, and therapeutic intervention. A preferred embodiment of the invention comprises clinical application of the information described herein to a patient. Diagnostic compositions, including microarrays, and methods can be designed to identify the genetic alterations described herein in nucleic acids from a patient to assess susceptibility for developing ADHD. This can occur after a patient arrives in the clinic; the patient has blood drawn, and using the diagnostic methods described herein, a clinician can detect a SNP in the genetic regions listed in Table 6 above. The typical age range for a patient to be screened is between 5 and 18 years of age. The information obtained from the patient sample (e.g., nucleic acids), which can optionally be amplified prior to assessment, will be used to diagnose a patient with an increased or decreased susceptibility for developing ADHD. Kits for performing the diagnostic method of the invention are also provided herein. Such kits comprise a microarray comprising at least one of the SNPs provided herein in and the necessary reagents for assessing the patient samples as described above. In an alternative embodiment, a multiplex SNP panel is employed and the patient sample is assessed for the presence or absence of all the SNPs described herein.

REFERENCES

1. Faraone S V, Sergeant J, Gillberg C, Biederman J The worldwide prevalence of ADHD: is it an American condition? *World Psychiatry* 2003; 2(2): 104-113.
2. Hawi Z, Cummins T D, Tong J, Johnson B, Lau R, Samarrai W et al. The molecular genetic architecture of attention deficit hyperactivity disorder. *Mol Psychiatry* 2015; 20(3): 289-297.
3. Mannuzza S, Klein R G, Bessler A, Malloy P, LaPadula M. Adult outcome of hyperactive boys. Educational achievement, occupational rank, and psychiatric status. *Arch Gen Psychiatry* 1993; 50(7): 565-576.
4. Faraone S V, Biederman J, Spencer T, Wilens T, Seidman L J, Mick E et al. Attention-deficit/hyperactivity disorder in adults: an overview. *Biol Psychiatry* 2000; 48(1): 9-20.
5. Kessler R C, Adler L A, Barkley R, Biederman J, Conners C K, Faraone S V et al. Patterns and predictors of attention-deficit/hyperactivity disorder persistence into adulthood: results from the national comorbidity survey replication. *Biol Psychiatry* 2005; 57(11): 1442-1451.
6. Faraone S V, Perlis R H, Doyle A E, Smoller J W, Goralnick J J, Holmgren M A et al. Molecular genetics of attention-deficit/hyperactivity disorder. *Biol Psychiatry* 2005; 57(11): 1313-1323.
7. Rietveld M J, Hudziak J J, Bartels M, van Beijsterveldt C E, Boomsma D I. Heritability of attention problems in children: I. cross-sectional results from a study of twins, age 3-12 years. *Am J Med Genet B Neuropsychiatr Genet* 2003; 117B(1): 102-113.
8. Franke B, Faraone S V, Asherson P, Buitelaar J, Bau C H, Ramos-Quiroga J A et al. The genetics of attention deficit/hyperactivity disorder in adults, a review. *Mol Psychiatry* 2012; 17(10): 960-987.
9. Elia J, Glessner J T, Wang K, Takahashi N, Shtir C J, Hadley D et al. Genome-wide copy number variation study associates metabotropic glutamate receptor gene networks with attention deficit hyperactivity disorder. *Nature genetics* 2011; 44(1): 78-84.
10. Elia J, Ungal G, Kao C, Ambrosini A, De Jesus-Rosario N, Larsen L et al. Fasoracetam in adolescents with ADHD and glutamatergic gene network variants disrupting mGluR neurotransmitter signaling. *Nature communications* 2018; 9(1): 4.
11. Neale B M, Lasky-Su J, Anney R, Franke B, Zhou K, Maller J B et al. Genome-wide association scan of attention deficit hyperactivity disorder. *Am J Med Genet B Neuropsychiatr Genet* 2008; 147B(8): 1337-1344.
12. Neale B M, Medland S, Ripke S, Anney R J, Asherson P, Buitelaar J et al. Case-control genome-wide association study of attention-deficit/hyperactivity disorder. *J Am Acad Child Adolesc Psychiatry* 2010; 49(9): 906-920.
13. Neale B M, Medland S E, Ripke S, Asherson P, Franke B, Lesch K P et al. Meta-analysis of genome-wide association studies of attention-deficit/hyperactivity disorder. *J Am Acad Child Adolesc Psychiatry* 2010; 49(9): 884-897.
14. Mick E, Todorov A, Smalley S, Hu X, Loo S, Todd R D et al. Family-based genome-wide association scan of attention-deficit/hyperactivity disorder. *J Am Acad Child Adolesc Psychiatry* 2010; 49(9): 898-905 e893.
15. Hinney A, Scherag A, Jarick I, Albayrak O, Putter C, Pechlivanis S et al. Genome-wide association study in German patients with attention deficit/hyperactivity disorder. *Am J Med Genet B Neuropsychiatr Genet* 2011; 156B(8): 888-897.
16. Stergiakouli E, Hamshere M, Holmans P, Langley K, Zaharieva I, de C G et al. Investigating the contribution of common genetic variants to the risk and pathogenesis of ADHD. *Am J Psychiatry* 2012; 169(2): 186-194.
17. Yang L, Neale B M, Liu L, Lee S H, Wray N R, Ji N et al. Polygenic transmission and complex neuro developmental network for attention deficit hyperactivity disorder: genome-wide association study of both common and rare variants. *Am J Med Genet* B Neuropsychiatr Genet 2013; 162B(5): 419-430.
18. Lesch K P, Timmesfeld N, Renner T J, Halperin R, Roser C, Nguyen T T et al. Molecular genetics of adult ADHD: converging evidence from genome-wide association and extended pedigree linkage studies. *J Neural Transm (Vienna)* 2008; 115(11): 1573-1585.
19. Chang C C, Chow C C, Tellier L C, Vattikuti S, Purcell S M, Lee J J. Second-generation PLINK: rising to the challenge of larger and richer datasets. *Gigascience* 2015; 4: 7.

20. Das S, Forer L, Schonherr S, Sidore C, Locke A E, Kwong A et al. Next-generation genotype imputation service and methods. *Nature genetics* 2016; 48(10): 1284-1287.
21. Loh P R, Danecek P, Palamara P F, Fuchsberger C, Y A R, H K F et al. Reference-based phasing using the Haplotype Reference Consortium panel. *Nature genetics* 2016; 48(11): 1443-1448.
22. Price A L, Patterson N J, Plenge R M, Weinblatt M E, Shadick N A, Reich D. Principal components analysis corrects for stratification in genome-wide association studies. *Nature genetics* 2006; 38(8): 904-909.
23. Marchini J, Howie B. Genotype imputation for genome-wide association studies. *Nature reviews Genetics* 2010; 11(7): 499-511.
24. Ward L D, Kellis M. HaploReg: a resource for exploring chromatin states, conservation, and regulatory motif alterations within sets of genetically linked variants. *Nucleic acids research* 2012; 40 (Database issue): D930-934.
25. Consortium G T. The Genotype-Tissue Expression (GTEx) project. *Nature genetics* 2013; 45(6): 580-585.
26. Ong B A, Li J, McDonough J M, Wei Z, Kim C, Chiavacci R et al. Gene network analysis in a pediatric cohort identifies novel lung function genes. *PloS one* 2013; 8(9): e72899.
27. Ng B, White C C, Klein H U, Sieberts S K, McCabe C, Patrick E et al. An xQTL map integrates the genetic architecture of the human brain's transcriptome and epigenome. *Nat Neurosci* 2017.
28. Sleiman P M, Flory J, Imielinski M, Bradfield J P, Annaiah K, Willis-Owen S A et al. Variants of DENND1B associated with asthma in children. *The New England journal of medicine* 2010; 362(1): 36-44.
29. Galanter J M, Gignoux C R, Torgerson D G, Roth L A, Eng C, Oh S S et al. Genome-wide association study and admixture mapping identify different asthma-associated loci in Latinos: the Genes-environments & Admixture in Latino Americans study. *The Journal of allergy and clinical immunology* 2014; 134(2): 295-305.
30. Lin P I, Vance J M, Pericak-Vance M A, Martin E R. No gene is an island: the flip-flop phenomenon. *American journal of human genetics* 2007; 80(3): 531-538.
31. Van Aller G S, Reynoird N, Barbash O, Huddleston M, Liu S, Zmoos A F et al. Smyd3 regulates cancer cell phenotypes and catalyzes histone H4 lysine 5 methylation. *Epigenetics* 2012; 7(4): 340-343.
32. Liu C, Wang C, Wang K, Liu L, Shen Q, Yan K et al. SMYD3 as an oncogenic driver in prostate cancer by stimulation of androgen receptor transcription. *J Natl Cancer Inst* 2013; 105(22): 1719-1728.
33. Zhu Y, Zhu M X, Zhang X D, Xu X E, Wu Z Y, Liao L D et al. SMYD3 stimulates EZR and LOXL2 transcription to enhance proliferation, migration, and invasion in esophageal squamous cell carcinoma. *Hum Pathol* 2016; 52: 153-163.
34. Huang L, Xu A M. SET and MYND domain containing protein 3 in cancer. *Am J Transl Res* 2017; 9(1): 1-14.
35. Day J J, Sweatt J D. DNA methylation and memory formation. *Nat Neurosci* 2010; 13(11): 1319-1323.
36. Guo J U, Ma D K, Mo H, Ball M P, Jang M H, Bonaguidi M A et al. Neuronal activity modifies the DNA methylation landscape in the adult brain. *Nat Neurosci* 2011; 14(10): 1345-1351.
37. Jones P A, Baylin S B. The epigenomics of cancer. *Cell* 2007; 128(4): 683-692.
38. Esteller M. Epigenetics in cancer. *The New England journal of medicine* 2008; 358(11): 1148-1159.
39. van Bokhoven H. Genetic and epigenetic networks in intellectual disabilities. *Annu Rev Genet* 2011; 45: 81-104.
40. Ronan J L, Wu W, Crabtree G R. From neural development to cognition: unexpected roles for chromatin. *Nature reviews Genetics* 2013; 14(5): 347-359.
41. Crawley J N, Heyer W D, LaSalle J M. Autism and Cancer Share Risk Genes, Pathways, and Drug Targets. *Trends Genet* 2016; 32(3): 139-146.
42. Lima Lde A, Feio-dos-Santos A C, Belangero S I, Gadelha A, Bressan R A, Salum G A et al. An integrative approach to investigate the respective roles of single-nucleotide variants and copy-number variants in Attention-Deficit/Hyperactivity Disorder. *Sci Rep* 2016; 6: 22851.
43. Okura Y, Urban L H, Mahoney D W, Jacobsen S J, Rodeheffer R J. Agreement between self-report questionnaires and medical record data was substantial for diabetes, hypertension, myocardial infarction and stroke but not for heart failure. *J Clin Epidemiol* 2004; 57(10): 1096-1103.
44. Almoguera B, Vazquez L, Mentch F, Connolly J, Pacheco J A, Sundaresan A S et al. Identification of Four Novel Loci in Asthma in European American and African American Populations. *American journal of respiratory and critical care medicine* 2017; 195(4): 456-463.
45. Newton K M, Peissig P L, Kho A N, Bielinski S J, Berg R L, Choudhary V et al. Validation of electronic medical record-based phenotyping algorithms results and lessons learned from the eMERGE network. *Journal of the American Medical Informatics Association: JAMIA* 2013; 20(e1): e147-154.

While certain of the preferred embodiments of the present invention have been described and specifically exemplified above, it is not intended that the invention be limited to such embodiments. It will be apparent to one skilled in the art that various changes and modifications can be made therein without departing from the scope of the present invention, as set forth in the following claims.

What is claimed is:

1. A method for identifying a therapeutic agent which alters neuronal signaling and/or neuronal cell morphology, comprising
   a) providing neuronal cells comprising an A allele of rs2105158;
   b) providing neuronal cells which lack said A allele and comprise C alleles of rs2105158;
   c) contacting the cells of steps a) and b) with a test agent; and
   d) after said contacting, measuring alterations in neuronal signaling and/or morphology of the neuronal cells of step a) relative to neuronal cells of step b); identifying the agent causing said alterations as a modulator of neuronal signaling and/or morphology.

2. The method of claim 1 wherein said therapeutic has efficacy for the treatment of ADHD or a neurodevelopmental disorder.

3. The method of claim 1, wherein said therapeutic agent is a SMYD3 inhibitor.

4. The method of claim 3, wherein said SMYD3 inhibitor is a siRNA which down modulates SMYD3 protein expression.

5. The method of claim 1, wherein said therapeutic agent is selected from stimulants, norepinephrine reuptake inhibitors, alpha-2 agonists, norepinephrine-dopamine reuptake inhibitors, and serotonin and norepinephrine reuptake inhibitors (SNRIs).

6. The method of claim 1, wherein said therapeutic agent is selected from Methylphenidate, dexmethylphenidate, amphetamines, Atomoxetine, Clonidine, guanfacine, Bupropion, Imipramine, melipramine, Carbamazepine, clonazepam, fluoxetine, hydroxyzine, lithium, olanzapine, paroxetine, pemoline, risperidone, sertraline, trazodone, and valproic acid.

* * * * *